US012708337B2

(12) United States Patent
Takemoto

(10) Patent No.: US 12,708,337 B2
(45) Date of Patent: Aug. 18, 2026

(54) MEDICAL IMAGE CAPTURING APPARATUS AND CONTROL METHOD OF THE SAME

(71) Applicant: FUJIFILM Healthcare Corporation, Chiba (JP)

(72) Inventor: Kazuma Takemoto, Kashiwa (JP)

(73) Assignee: FUJIFILM Corporation, Tokyo (JP)

( * ) Notice: Subject to any disclaimer, the term of this patent is extended or adjusted under 35 U.S.C. 154(b) by 178 days.

(21) Appl. No.: 18/429,268

(22) Filed: Jan. 31, 2024

(65) Prior Publication Data

US 2024/0268777 A1 Aug. 15, 2024

(30) Foreign Application Priority Data

Feb. 14, 2023 (JP) ................................ 2023-020646

(51) Int. Cl.

*A61B 6/00* (2024.01)
*A61B 6/04* (2006.01)
*A61B 6/46* (2024.01)

(52) U.S. Cl.

CPC .......... *A61B 6/5235* (2013.01); *A61B 6/0407* (2013.01); *A61B 6/463* (2013.01); *A61B 6/547* (2013.01)

(58) Field of Classification Search

CPC ..... A61B 6/5235; A61B 6/463; A61B 6/0407; A61B 6/032; A61B 6/547; A61B 6/5247; A61B 6/5211

See application file for complete search history.

(56) References Cited

U.S. PATENT DOCUMENTS

2015/0313566 A1* 11/2015 Diers ..................... A61B 6/505 378/63
2016/0074004 A1* 3/2016 Braun ..................... G06F 3/017 378/205
2016/0174930 A1* 6/2016 Braun ..................... A61B 6/03 378/205
2016/0361035 A1* 12/2016 Lee ........................ A61B 6/469
2017/0049529 A1* 2/2017 Hannemann ............. A61B 5/70
2017/0224298 A1* 8/2017 Hannemann ........... A61B 6/469
2017/0228877 A1* 8/2017 Ito .......................... A61B 34/10
2017/0249423 A1* 8/2017 Wang ................. G06V 10/7557
2017/0281109 A1* 10/2017 Ecabert ................ A61B 6/5205

(Continued)

FOREIGN PATENT DOCUMENTS

JP 2006288908 10/2006

*Primary Examiner* — David J Makiya
*Assistant Examiner* — Soorena Kefayati
(74) *Attorney, Agent, or Firm* — JCIPRNET

(57) ABSTRACT

There is provided a medical image capturing apparatus including a table on which a subject is placed, a scan gantry unit that includes a detection unit which detects a signal obtained from the subject, an image generation unit that generates a medical image by using a detection signal transmitted from the detection unit, a display unit that displays the medical image, a camera that images the subject on the table, and a processor. The processor designates an imaging position with respect to the subject before movement of the table, acquires a camera image captured by the camera before, during, or after the movement of the table, and generates a superimposed image in which the imaging position is superimposed on the camera image and displays the superimposed image on the display unit.

5 Claims, 10 Drawing Sheets

(56) References Cited

U.S. PATENT DOCUMENTS

| | | | | |
|---|---|---|---|---|
| 2019/0321657 | A1* | 10/2019 | Hale | A61N 5/1049 |
| 2019/0343479 | A1* | 11/2019 | Sato | A61B 6/06 |
| 2020/0036910 | A1* | 1/2020 | Alzaga | G06T 7/70 |
| 2020/0237332 | A1* | 7/2020 | Wang | A61B 6/5241 |
| 2020/0268339 | A1* | 8/2020 | Hao | A61B 6/544 |
| 2022/0265228 | A1* | 8/2022 | Shimizu | A61B 6/04 |
| 2022/0273256 | A1* | 9/2022 | Sugahara | A61B 6/54 |
| 2022/0287672 | A1* | 9/2022 | Matsuura | G06T 7/337 |
| 2022/0287676 | A1* | 9/2022 | Steines | A61B 90/37 |

* cited by examiner

MEDICAL IMAGE CAPTURING APPARATUS AND CONTROL METHOD OF THE SAME

CLAIM OF PRIORITY

The present application claims priority from Japanese Patent Application JP 2023-020646 filed on Feb. 14, 2023, the content of which is hereby incorporated by reference into this application.

BACKGROUND OF THE INVENTION

1. Field of the Invention

The present invention relates to a medical image capturing apparatus that captures a medical image of a subject, and particularly, to a technique of confirming an imaging position designated with respect to the subject.

2. Description of the Related Art

A medical image capturing apparatus is an apparatus that detects a signal obtained from a subject, for example, X-rays transmitted through the subject, nuclear magnetic resonance signals generated from the subject, or the like, with a detection unit to capture a medical image to be used to diagnose the subject, or the like. In the medical image capturing apparatus, an imaging position is designated with respect to the subject on a table prior to the capturing of the medical image, and the designated imaging position is aligned with the detection unit through the movement of the table.

In JP2006-288908A, it is disclosed that, in a case where an imaging position is designated in a camera image obtained by imaging a subject on a table, position coordinates of the imaging position on the table are obtained, and the position coordinates are moved to a position of a detection unit by using the table, in order to quickly align the imaging position with the detection unit.

SUMMARY OF THE INVENTION

However, JP2006-288908A lacks consideration for confirming the designated imaging position in the camera image after a start of movement of the table. An operator in an operation room can confirm a state of the subject through the camera image, but it becomes difficult to confirm the imaging position after the table starts moving. In particular, in a case where the table enters a scan gantry unit including the detection unit, it becomes more difficult to confirm the imaging position.

In that respect, an object of the present invention is to provide a medical image capturing apparatus and a control method of the same that enable confirmation of an imaging position designated with respect to a subject even after a start of movement of a table.

In order to achieve the above-described object, according to an aspect of the present invention, there is provided a medical image capturing apparatus comprising: a table on which a subject is placed; a scan gantry unit that includes a detection unit which detects a signal obtained from the subject; an image generation unit that generates a medical image by using a detection signal transmitted from the detection unit; a display unit that displays the medical image; a camera that images the subject on the table; and an imaging position designation unit that designates an imaging position with respect to the subject before movement of the table, in which the medical image capturing apparatus further includes: a camera image acquisition unit that acquires a camera image captured by the camera before, during, or after the movement of the table; and a superimposed image generation unit that generates a superimposed image in which the imaging position is superimposed on the camera image and displays the superimposed image on the display unit.

In addition, according to another aspect of the present invention, there is provided a control method of a medical image capturing apparatus including a table on which a subject is placed, a scan gantry unit that includes a detection unit which detects a signal obtained from the subject, an image generation unit that generates a medical image by using a detection signal transmitted from the detection unit, a display unit that displays the medical image, a camera that images the subject on the table, and an imaging position designation unit that designates an imaging position with respect to the subject before movement of the table, the control method comprising: a camera image acquisition step of acquiring a camera image captured by the camera before, during, or after the movement of the table; and a superimposed image generation step of generating a superimposed image in which the imaging position is superimposed on the camera image and displaying the superimposed image on the display unit.

According to the aspects of the present invention, it is possible to provide a medical image capturing apparatus and a control method of the same that enable confirmation of an imaging position designated with respect to a subject even after a start of movement of a table.

DESCRIPTION OF THE PREFERRED EMBODIMENTS

Hereinafter, examples of a medical image capturing apparatus according to the present invention will be described with reference to the accompanying drawings. The medical image capturing apparatus is an apparatus that detects a signal obtained from a subject, for example, X-rays transmitted through the subject, nuclear magnetic resonance signals generated from the subject, or the like, to capture a medical image to be used to diagnose the subject, or the like. Hereinafter, as an example of the medical image capturing apparatus, an X-ray computed tomography (CT) apparatus that captures a tomographic image of the subject by acquiring X-ray projection images of the subject at various projection angles will be described.

Example 1

Figure 1:
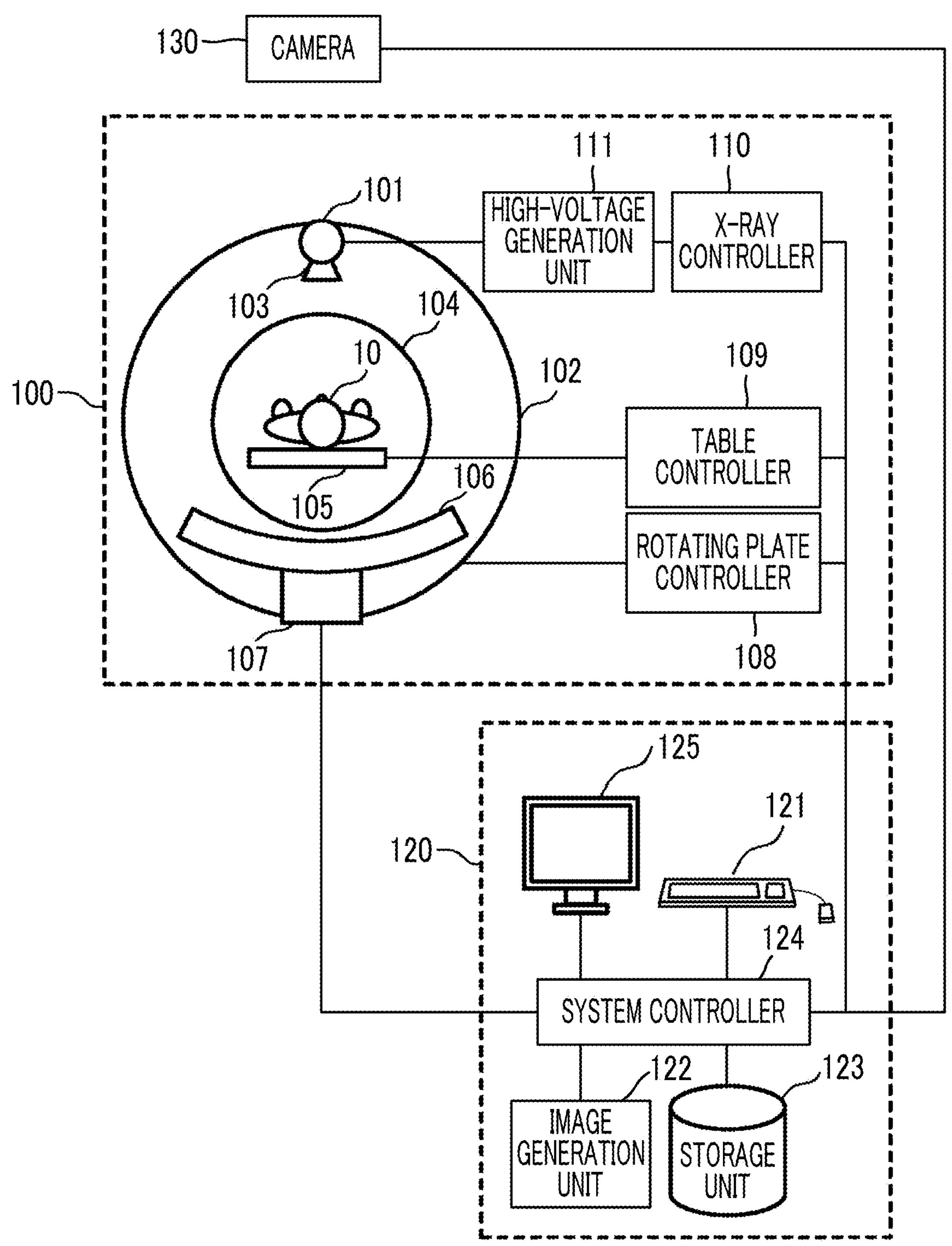
FIG. 1 is a diagram showing an example of an overall configuration of an X-ray CT apparatus of Example 1.

An overall configuration of the X-ray CT apparatus of Example 1 will be described with reference to FIG. 1. The X-ray CT apparatus comprises a scan gantry unit 100, an operation unit 120, and a camera 130. The scan gantry unit 100 and the camera 130 are installed in an imaging room surrounded by a shielding material that blocks X-rays, and the operation unit 120 is installed in an operation room located outside the imaging room.

The scan gantry unit 100 comprises an X-ray source 101, a rotating plate 102, a collimator 103, an X-ray detector 106, a data collection unit 107, a table 105, a rotating plate controller 108, a table controller 109, an X-ray controller 110, and a high-voltage generation unit 111. The X-ray source 101 is a device that irradiates a subject 10 placed on the table 105 with X-rays and is, for example, an X-ray tube device. The collimator 103 is a device that restricts an irradiation range of X-rays. The rotating plate 102 is provided with an opening portion 104 through which the subject 10 placed on the table 105 enters, and is also equipped with the X-ray source 101 and the X-ray detector 106 and rotates the X-ray source 101 and the X-ray detector 106 around the subject 10.

The X-ray detector 106 is a device that is disposed to face the X-ray source 101, that comprises a plurality of detection elements which detect X-rays transmitted through the subject 10, and that detects a spatial distribution of X-rays, and functions as a detection unit that detects a signal obtained from the subject 10. The detection elements of the X-ray detector 106 are arranged two-dimensionally in a rotation direction and a rotation axis direction of the rotating plate 102. The data collection unit 107 is a device that collects the spatial distribution of X-rays detected by the X-ray detector 106 as digital data.

The rotating plate controller 108 is a device that controls rotation and inclination of the rotating plate 102. The table controller 109 is a device that controls up, down, front, back, left, and right movements of the table 105. The high-voltage generation unit 111 is a device that generates a high voltage applied to the X-ray source 101. The X-ray controller 110 is a device that controls an output of the high-voltage generation unit 111. The rotating plate controller 108, the table controller 109, and the X-ray controller 110 are, for example, a micro-processing unit (MPU) or the like.

The operation unit 120 comprises an input unit 121, an image generation unit 122, a display unit 125, a storage unit 123, and a system controller 124. The input unit 121 is a device that is used to input examination data such as a name of the subject 10, an examination date and time, and an imaging condition, and is, for example, a keyboard, a pointing device, a touch panel, or the like. The image generation unit 122 is a device that generates the tomographic image by using the digital data collected by the data collection unit 107, and is, for example, an MPU, a graphics processing unit (GPU), or the like. The display unit 125 is a device that displays the tomographic image or the like generated by the image generation unit 122, and is, for example, a liquid crystal display, a touch panel, or the like. The storage unit 123 is a device that stores the digital data collected by the data collection unit 107, the tomographic image generated by the image generation unit 122, a program to be executed by the system controller 124, data to be used by the program, and the like, and is, for example, a hard disk drive (HDD), a solid state drive (SSD), or the like. The system controller 124 is a device that controls each unit such as the rotating plate controller 108, the table controller 109, and the X-ray controller 110, and is, for example, a central processing unit (CPU).

The camera 130 is a device that images the subject 10 placed on the table 105 together with the table 105 from above, and is provided on a ceiling of the imaging room or above the scan gantry unit 100. A camera image captured by the camera 130 is displayed on the display unit 125, and is used by an operator in the operation room to confirm a state of the subject 10 or is used to designate the imaging position. The camera image may be stored in the storage unit 123.

The high-voltage generation unit 111 generates a tube voltage, which is a high voltage applied to the X-ray source 101, based on the imaging condition set via the input unit 121, whereby X-rays corresponding to the imaging condition are emitted to the subject 10 from the X-ray source 101. The X-ray detector 106 detects the X-rays emitted from the X-ray source 101 and transmitted through the subject 10 with a large number of detection elements and acquires the spatial distribution of the transmitted X-rays. The rotating plate 102 is controlled by the rotating plate controller 108 and rotates based on the imaging condition input through the input unit 121, particularly a rotation speed or the like. The table 105 is controlled by the table controller 109 and moves relative to the rotating plate 102 to move the imaging position designated with respect to the subject 10 to an imaging field of view, which is a range in which the transmitted X-rays are detected.

By repeating the irradiation of X-rays by the X-ray source 101 and the detection of X-rays by the X-ray detector 106 with the rotation of the rotating plate 102, projection data, which is the X-ray projection image of the subject 10, is measured at various projection angles. The projection data is associated with a view representing each projection angle, and a channel (ch) number and a column number which are detection element numbers of the X-ray detector 106. The measured projection data is transmitted to the image generation unit 122. The image generation unit 122 generates the tomographic image by performing back-projection processing on a plurality of pieces of projection data. The generated tomographic image is displayed on the display unit 125 or stored in the storage unit 123 as the medical image.

It is difficult to confirm the imaging position, which is designated with respect to the subject 10 prior to the capturing of the tomographic image, after the table 105 starts moving. In that respect, in Example 1, a superimposed image in which the imaging position is superimposed on the camera image captured immediately before the start of movement of the table 105 is displayed on the display unit 125, thereby enabling confirmation of the imaging position even after the start of movement of the table 105.

Figure 2:
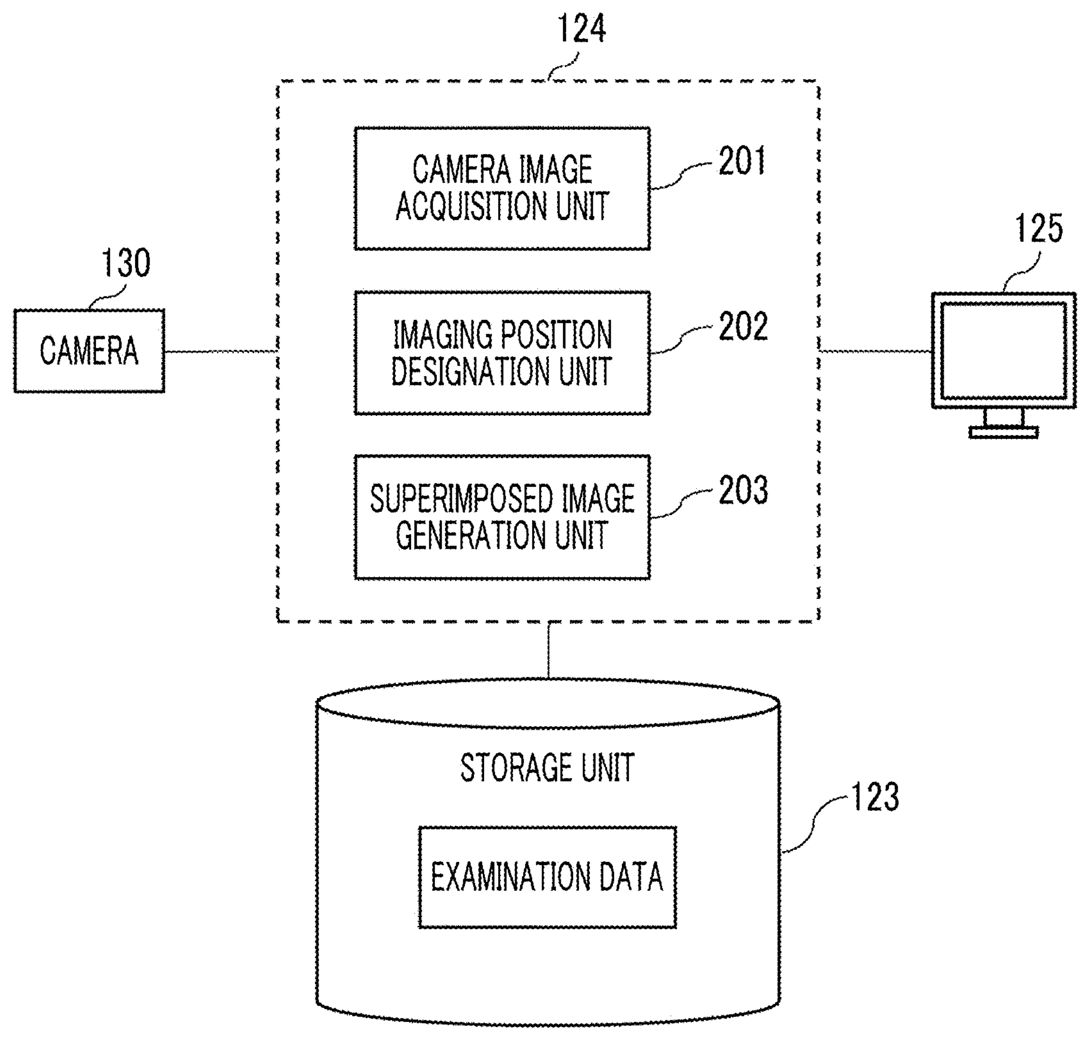
FIG. 2 is a diagram showing an example of functional blocks of Example 1.

The functional blocks of Example 1 will be described with reference to FIG. 2. It should be noted that these functional blocks may be configured with dedicated hardware using an application specific integrated circuit (ASIC), a field-programmable gate array (FPGA), or the like, or may be configured with software that operates on the system controller 124. In the following description, a case where the functional blocks of Example 1 are configured with software will be described.

In Example 1, a camera image acquisition unit 201, an imaging position designation unit 202, and a superimposed image generation unit 203 are provided. Hereinafter, each unit will be described. The storage unit 123 may store examination data related to the capturing of the medical image. The examination data includes the name of the subject 10, an examination site, imaging conditions, and the like.

The camera image acquisition unit 201 acquires the camera image captured by the camera 130. The acquired camera image is a digitized image and is a still image or a video.

The imaging position designation unit 202 designates the imaging position with respect to the subject 10. The imaging position may be designated based on the camera image acquired by the camera image acquisition unit 201. For example, the imaging position designation unit 202 may receive a position designated by the operator using the input unit 121 on the camera image, which is a still image, as the imaging position. In addition, the imaging position designation unit 202 may designate the imaging position based on the examination site and a shape of the subject 10 extracted from the camera image. More specifically, in a case where the examination site is a chest part, the imaging position designation unit 202 designates the imaging position based on the positions of the jaw and the shoulders estimated from the shape of the subject 10 on the camera image. Further, the imaging position designation unit 202 may be a machine learning engine that has been trained through machine learning using a shape of a human body and an imaging position for each examination site.

The superimposed image generation unit 203 generates the superimposed image in which the imaging position designated by the imaging position designation unit 202 is superimposed on the camera image acquired by the camera image acquisition unit 201 and displays the superimposed image on the display unit 125. The examination data or the like may be further superimposed on the superimposed image.

Figure 3:
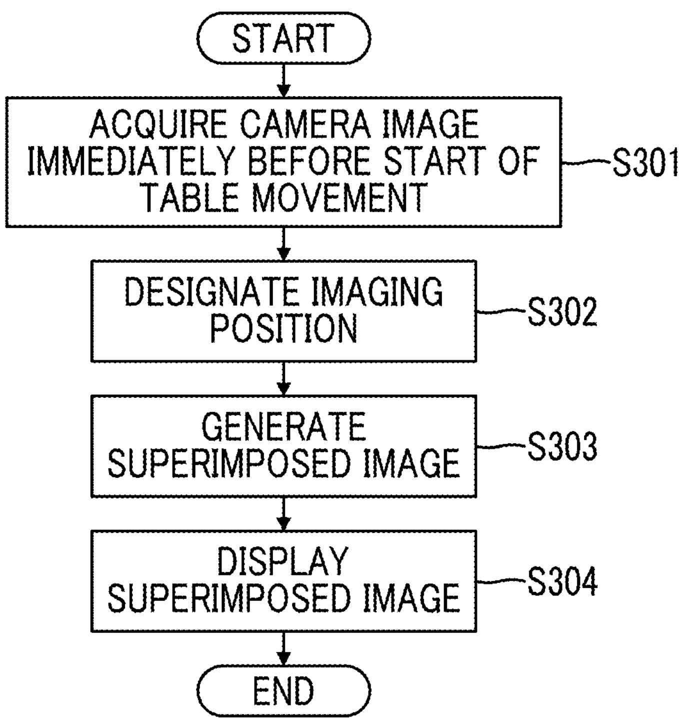
FIG. 3 is a diagram showing an example of a flow of processing of Example 1.

An example of a flow of processing of Example 1 will be described step by step with reference to FIG. 3.

S301

Figure 4:
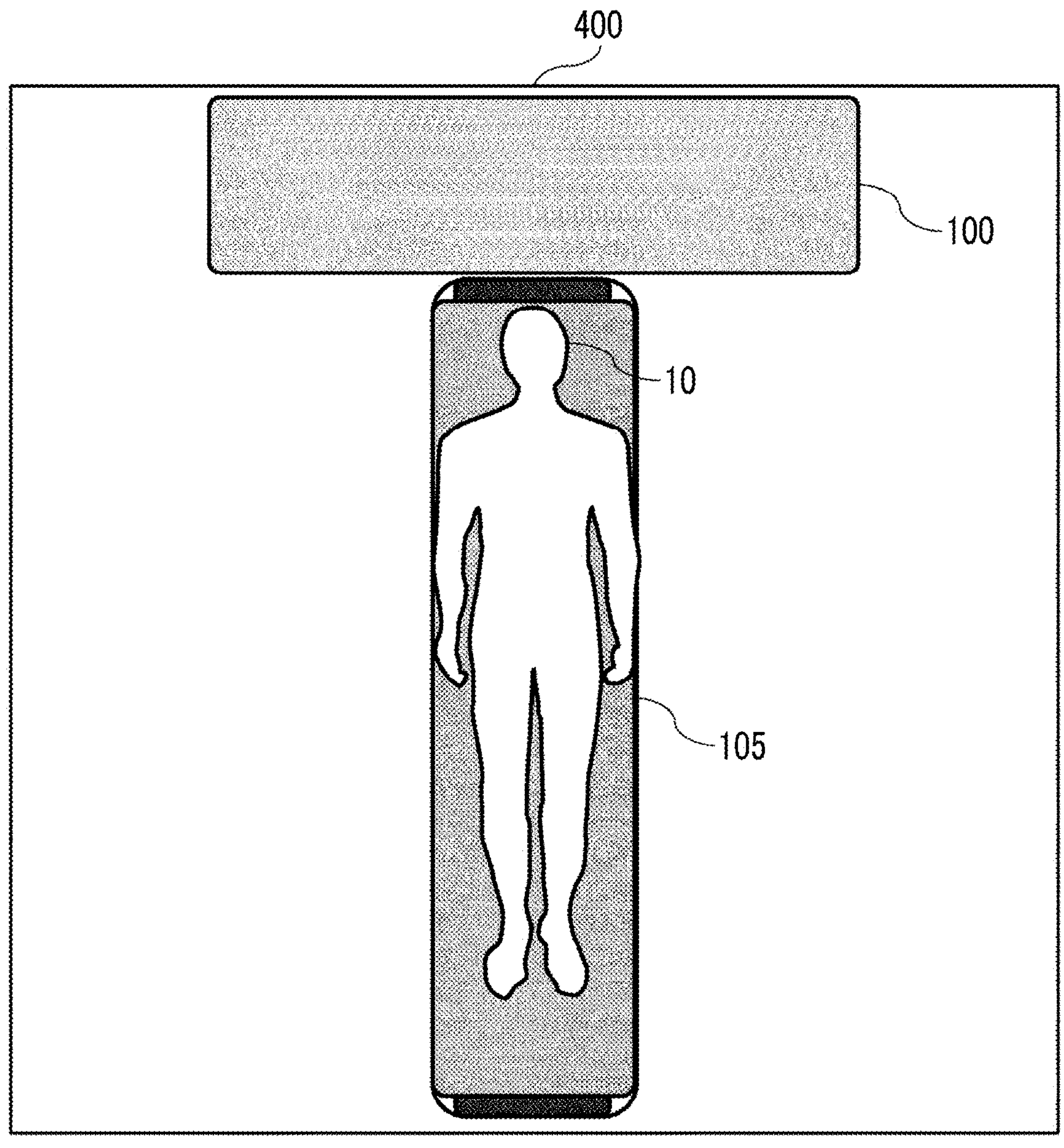
FIG. 4 is a diagram showing an example of a camera image immediately before table movement.

The camera image acquisition unit 201 acquires the camera image captured immediately before the table 105 starts moving. The camera image acquired in S301 is a still image, and may be a camera image transmitted from the camera 130 or a camera image read out from the storage unit 123. FIG. 4 shows an example of the camera image acquired in S301. A camera image 400 illustrated in FIG. 4 includes the scan gantry unit 100, as well as the subject 10 and the table 105 before entering the opening portion 104 of the scan gantry unit 100.

S302

The imaging position designation unit 202 designates the imaging position with respect to the subject 10 by using the camera image acquired in S301. The imaging position may be a position designated by the operator using the input unit 121 on the camera image 400, or may be a position designated based on the examination site and the shape of the subject 10 extracted from the camera image 400.

S303

The superimposed image generation unit 203 generates the superimposed image in which the imaging position designated in S302 is superimposed on the camera image 400 acquired in S301.

Figure 5:
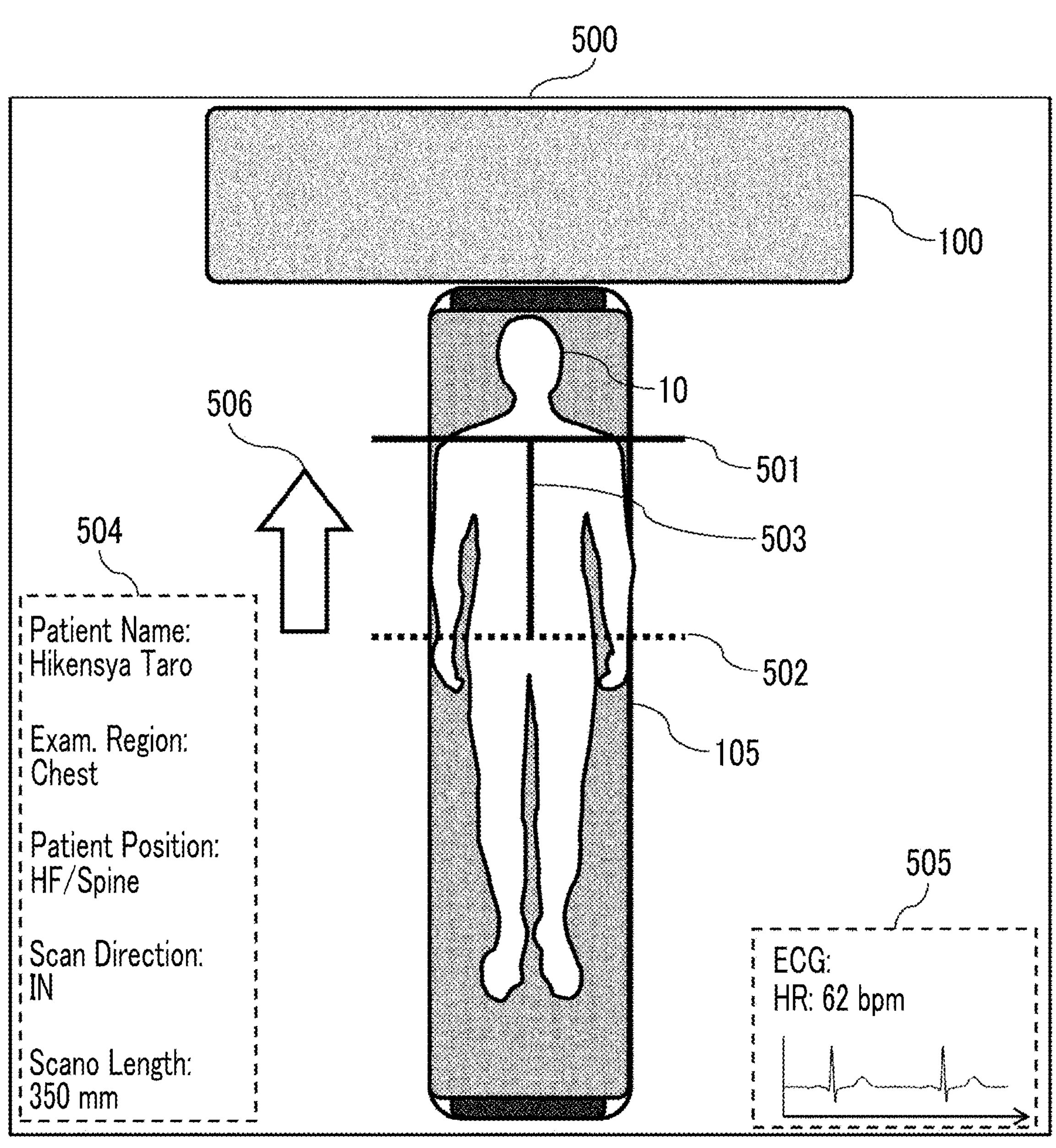
FIG. 5 is a diagram showing an example of a superimposed image of Example 1.

FIG. 5 shows an example of the superimposed image generated in S303. On a superimposed image 500 illustrated in FIG. 5, the imaging positions, such as an imaging start position 501, an imaging end position 502, and an imaging center position 503, on the scan gantry unit 100, the subject 10, or the table 105 included in the camera image 400 are superimposed. Additionally, on the superimposed image 500, examination data 504 including the name of the subject 10, the examination site, the imaging conditions, and the like, electrocardiogram data 505 of the subject 10, and a table movement direction 506 indicating a direction in which the table 105 moves may be further superimposed.

S304

The superimposed image generation unit 203 displays the superimposed image generated in S303 on the display unit 125. The superimposed image may be displayed not only on the display unit 125 of the operation unit 120 but also on a liquid crystal display or the like provided in the scan gantry unit 100.

Through the flow of the processing described with reference to FIG. 3, the superimposed image in which the imaging position designated with respect to the subject 10 is superimposed on the camera image obtained by imaging the subject 10 immediately before the start of movement of the table 105 is displayed on the display unit 125. By displaying the superimposed image, the operator can confirm the imaging position even after the start of movement of the table 105.

Example 2

In Example 1, displaying the superimposed image in which the imaging position is superimposed on the camera image captured immediately before the start of movement of the table 105 has been described. In Example 2, displaying a superimposed image in which the imaging position is superimposed on a camera image captured during or after the movement of the table 105 will be described. Since some of the configurations or functions described in will be omitted.

Figure 6:
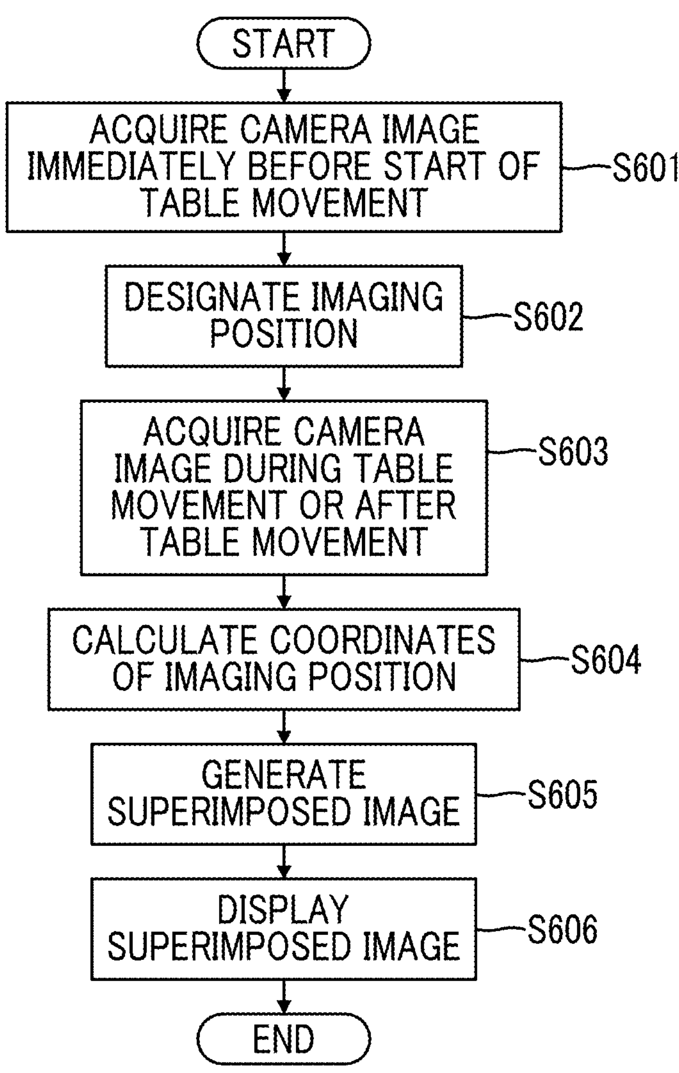
FIG. 6 is a diagram showing an example of a flow of processing of Example 2.

An example of a flow of processing of Example 2 will be described step by step with reference to FIG. 6. The description of the same processing as in Example 1 will be simplified.

S601 and S602

S601 and S602 are the same as S301 and S302 of Example 1.

S603

The camera image acquisition unit 201 acquires the camera image captured during or after the movement of the table 105.

S604

The superimposed image generation unit 203 calculates coordinates of the imaging position in the camera image acquired in S603. For example, based on a difference between a pre-movement image, which is the camera image used to designate the imaging position, and a post-movement image, which is the camera image acquired in S603, the coordinates of the imaging position in the post-movement image are calculated. More specifically, an outer shape of the subject 10 or the table 105 is extracted from each of the pre-movement image and the post-movement image, and an amount of positional shift of the outer shape of the post-movement image with respect to the outer shape of the pre-movement image is calculated. Then, by adding the calculated amount of positional shift to the coordinates of the imaging position in the pre-movement image, the coordinates of the imaging position in the post-movement image are calculated. In a case where the amount of positional shift of the outer shape of the subject 10 is used, the imaging position can be obtained more accurately even in a case where the subject 10 moves during the movement of the table 105. In addition, in a case where the amount of positional shift of the outer shape of the table 105 is used, an amount of calculation can be reduced, so that the imaging position can be obtained more quickly.

S605

Figure 7:
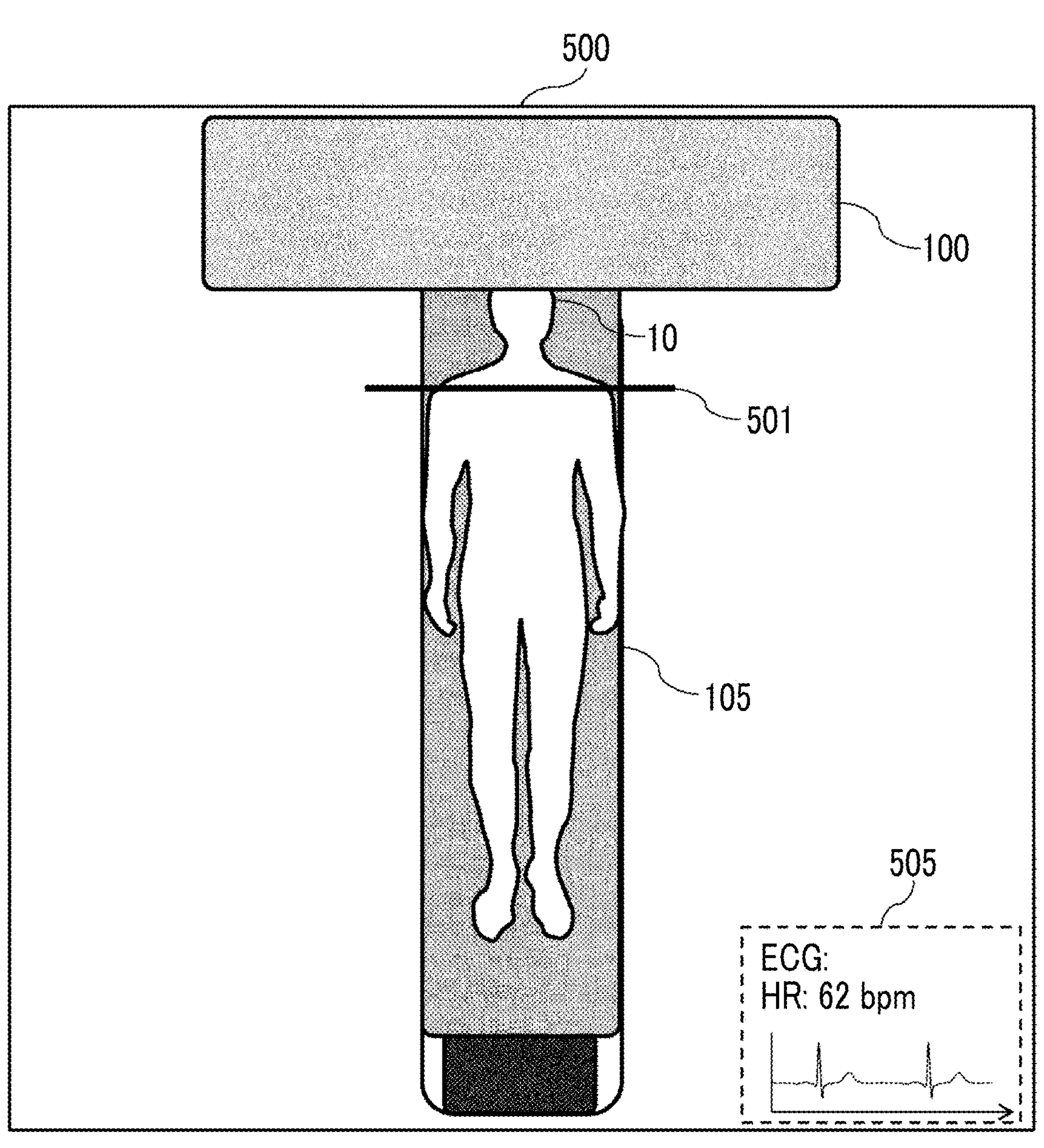
FIG. 7 is a diagram showing an example of a superimposed image during table movement.
Figure 8:
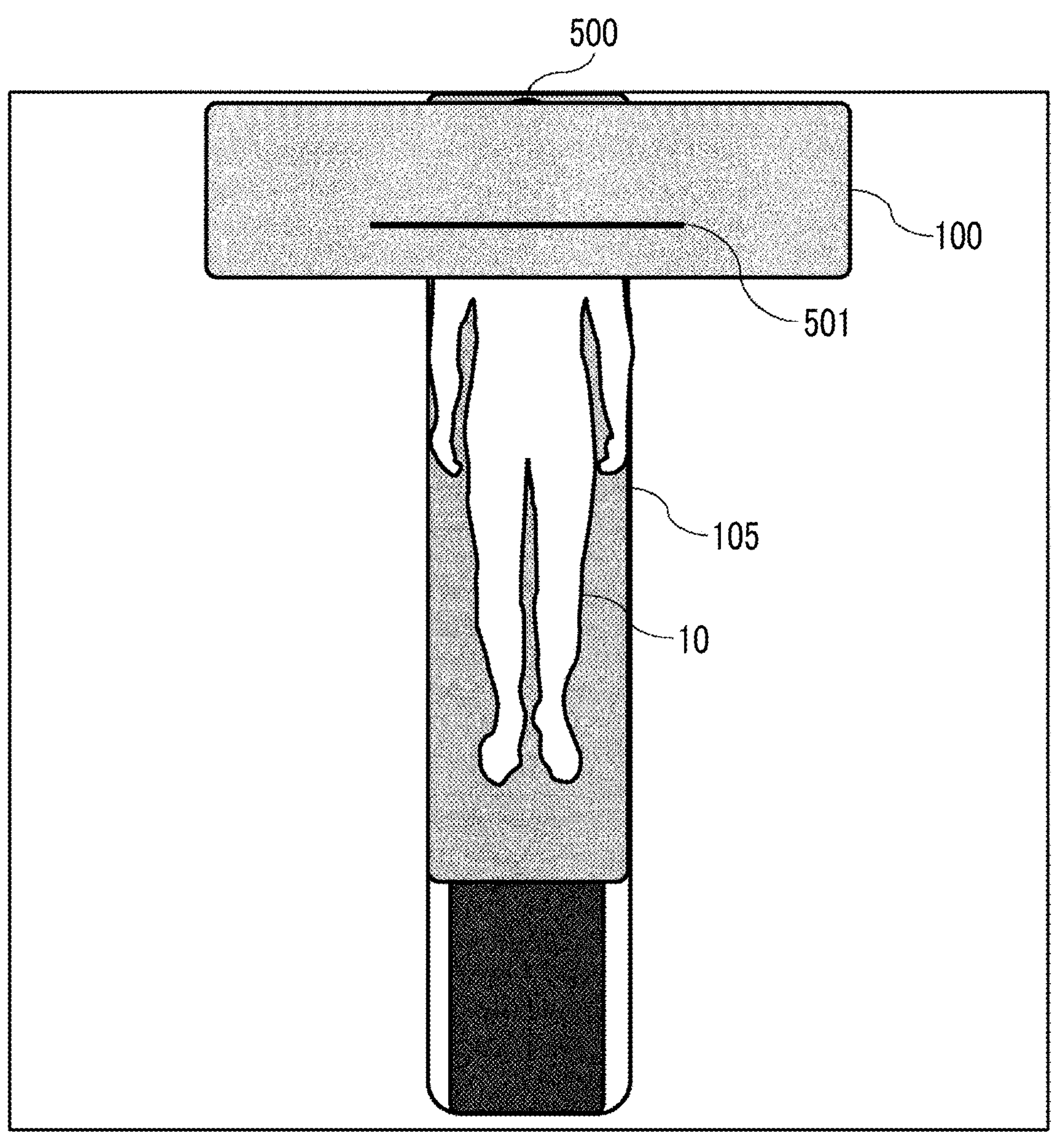
FIG. 8 is a diagram showing an example of a superimposed image after table movement.

The superimposed image generation unit 203 generates the superimposed image in which the imaging position designated in S602 is superimposed on the camera image acquired in S603, based on the coordinates calculated in S604. FIGS. 7 and 8 show examples of the superimposed image generated in S605.

The superimposed image 500 illustrated in FIG. 7 is an image in which the imaging start position 501 is superimposed on the camera image captured during the movement of the table 105. In addition, after the camera image during the movement of the table 105 is acquired as a video, the electrocardiogram data 505 of the subject 10 acquired together with the video may be displayed in synchronization with the superimposed image generated based on the video. By displaying the electrocardiogram data 505 in synchronization with the superimposed image generated based on the video, it is possible, for example, to perform imaging at the same cardiac phase at the time of a re-examination.

The superimposed image 500 illustrated in FIG. 8 is an image in which the imaging start position 501 is superimposed on the camera image captured after the table 105 has moved into the opening portion 104 of the scan gantry unit 100. The imaging position can be confirmed from the superimposed image illustrated in FIG. 8 even in a case where the subject 10 is hidden in the scan gantry unit 100.

S606

The superimposed image generation unit 203 displays the superimposed image generated in S605 on the display unit 125. The outer shape of the subject 10 or the imaging field of view of the scan gantry unit 100 may be further superimposed on the superimposed image together with the imaging position.

Figure 9:
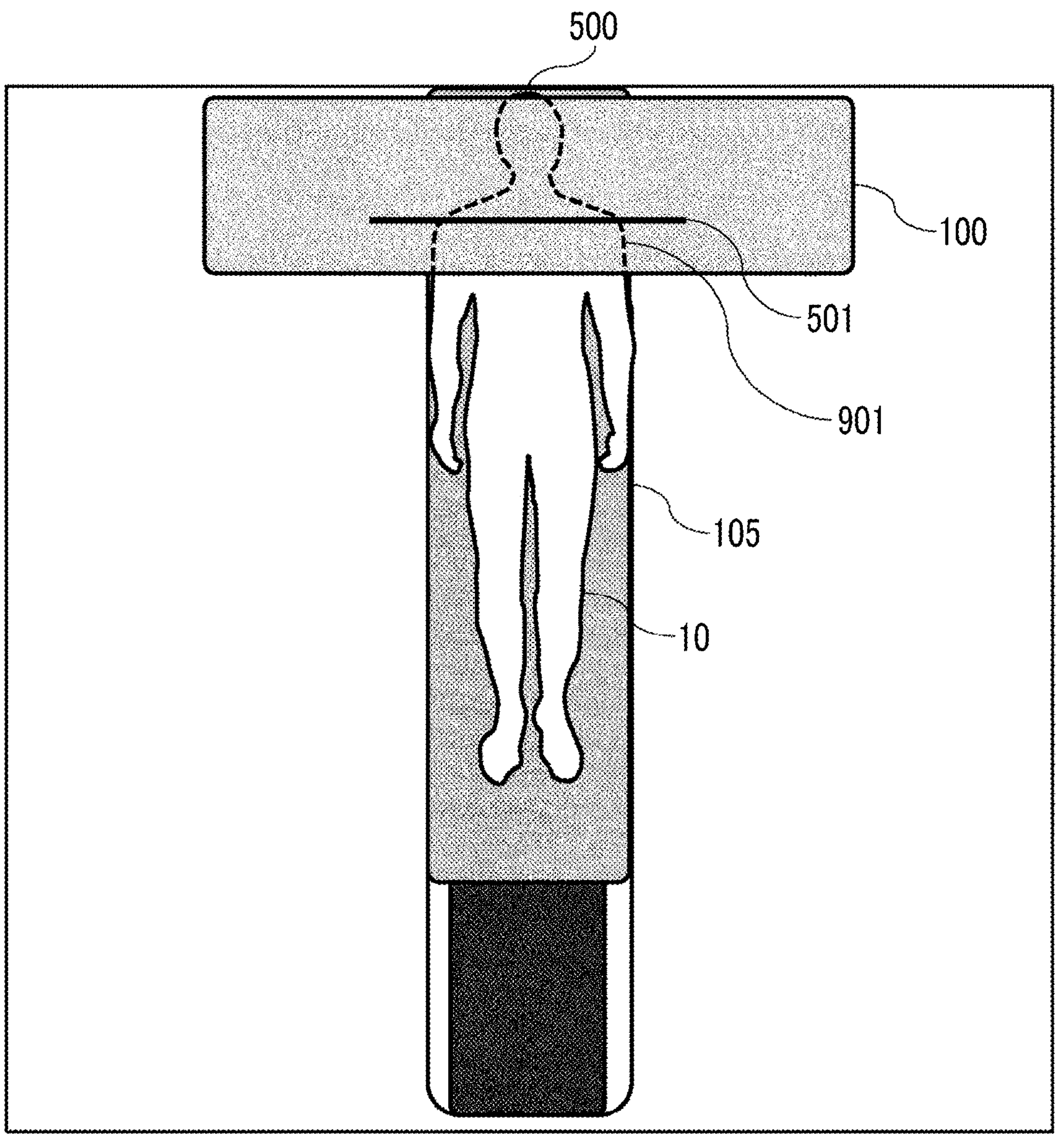
FIG. 9 is a diagram showing another example of the superimposed image after table movement.

The superimposed image 500 illustrated in FIG. 9 is an image in which the subject's outer shape 901 is superimposed on the camera image captured after the movement of the table 105 together with the imaging start position 501. By displaying the subject's outer shape 901 together with the imaging position, it becomes easier for the operator to confirm the imaging position designated with respect to the subject 10 hidden in the scan gantry unit 100.

Figure 10:
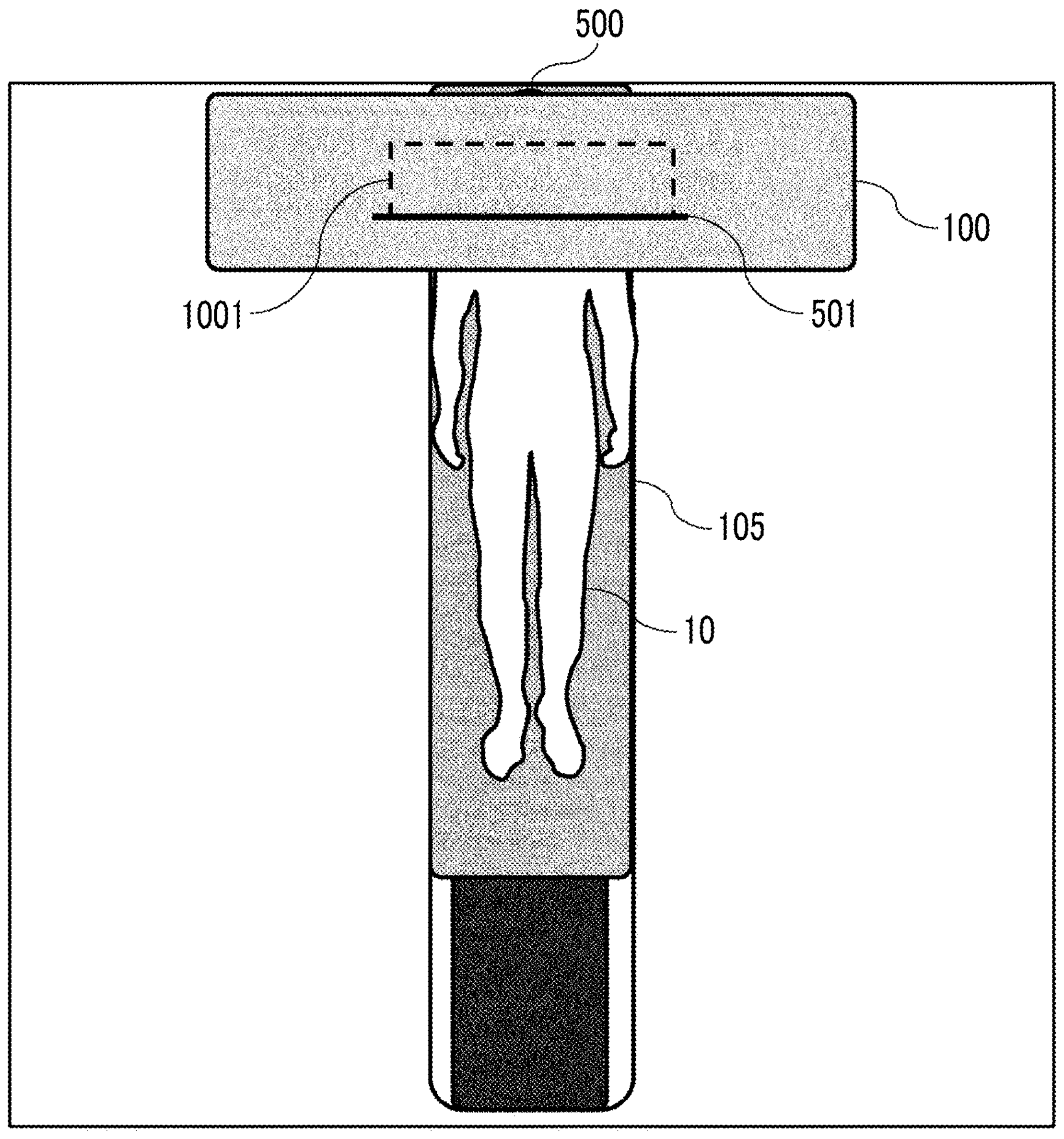
FIG. 10 is a diagram showing still another example of the superimposed image after table movement.

The superimposed image 500 illustrated in FIG. 10 is an image in which an imaging field of view 1001 of the scan gantry unit 100 is superimposed on the camera image captured after the movement of the table 105 together with the imaging start position 501. By displaying the imaging field of view 1001 together with the imaging position, the operator can confirm whether or not the imaging position has reached the imaging field of view through the movement of the table 105.

Through the flow of the processing described with reference to FIG. 6, the superimposed image in which the imaging position is superimposed on the camera image obtained by imaging the subject 10 during or after the movement of the table 105 is displayed on the display unit 125. By displaying the superimposed image, the operator can confirm the imaging position designated with respect to the subject 10 during or after the movement of the table 105.

The plurality of embodiments of the present invention have been described above. The present invention is not limited to the above-described embodiments, and the components can be modified and embodied without departing from the gist of the invention. Additionally, a plurality of components disclosed in the above-described embodiments may be combined as appropriate. For example, the imaging field of view 1001 of FIG. 10 may be further superimposed on the superimposed image illustrated in FIG. 9. Furthermore, some components may be deleted from all the components described in the above-described embodiments.

EXPLANATION OF REFERENCES

10: subject
100: scan gantry unit
101: X-ray source
102: rotating plate
103: collimator
104: opening portion
105: table
106: X-ray detector
107: data collection unit
108: rotating plate controller
109: table controller
110: X-ray controller
111: high-voltage generation unit
120: operation unit
121: input unit
122: image generation unit
123: storage unit
124: system controller
125: display unit
130: camera
201: camera image acquisition unit
202: imaging position designation unit
203: superimposed image generation unit
400: camera image
500: superimposed image
501: imaging start position
502: imaging end position
503: imaging center position
504: examination data
505: electrocardiogram data
506: table movement direction
901: subject's outer shape
1001: imaging field of view

What is claimed is:

1. A medical image capturing apparatus comprising:
a table on which a subject is placed;
a scan gantry unit that includes a detection unit which detects X-rays transmitted through the subject;
an image generation unit that generates a medical image by using a detection signal transmitted from the detection unit;
a display unit that displays the medical image;
a camera that images the subject on the table; and
a processor, configured to:
designate an imaging position with respect to the subject before movement of the table;
acquire a camera image captured by the camera during the movement of the table; and
generate a superimposed image in which the designated imaging position is superimposed on the subject in the camera image and displays the superimposed image on the display unit,
wherein the processor acquires the camera image during the movement of the table as a video and displays electrocardiogram data of the subject on the display unit in synchronization with the superimposed image generated based on the video.

2. The medical image capturing apparatus according to claim 1, wherein the processor designates the imaging position based on a pre-movement image, which is a camera image captured by the camera before the movement of the table, and the processor generates the superimposed image by calculating coordinates of the imaging position in a post-movement image, which is the camera image during the movement of the table or a camera image captured by the camera after the movement of the table, based on a difference between the post-movement image and the pre-movement image.

3. The medical image capturing apparatus according to claim 2, wherein the processor further superimposes an outer shape of the subject on the superimposed image.

4. The medical image capturing apparatus according to claim 2, wherein the processor further superimposes an imaging field of view of the scan gantry unit on the superimposed image.

5. A control method of a medical image capturing apparatus including a table on which a subject is placed, a scan gantry unit that includes a detection unit which detects X-rays transmitted through the subject, an image generation unit that generates a medical image by using a detection signal transmitted from the detection unit, a display unit that displays the medical image, and a camera that images the subject on the table, the control method comprising:

acquiring a camera image captured by the camera during the movement of the table; and generating a superimposed image in which an imaging position is superimposed on the camera image and displaying the superimposed image on the display unit, wherein the imaging position is designated with respect to the subject before movement of the table, wherein the camera image during the movement of the table is acquired as a video, and electrocardiogram data of the subject is displayed on the display unit in synchronization with the superimposed image generated based on the video.

* * * * *